(12) United States Patent
Aoki et al.

(10) Patent No.: US 8,461,380 B2
(45) Date of Patent: Jun. 11, 2013

(54) METHOD FOR PRODUCTION OF ACRYLIC ACID

(75) Inventors: Takanori Aoki, Kawasaki (JP); Norihide Arai, Oita (JP)

(73) Assignee: Showa Denko K.K., Tokyo (JP)

( * ) Notice: Subject to any disclaimer, the term of this patent is extended or adjusted under 35 U.S.C. 154(b) by 302 days.

(21) Appl. No.: 12/810,467

(22) PCT Filed: Dec. 15, 2008

(86) PCT No.: PCT/JP2008/072798
§ 371 (c)(1),
(2), (4) Date: Jun. 24, 2010

(87) PCT Pub. No.: WO2009/084417
PCT Pub. Date: Jul. 9, 2009

(65) Prior Publication Data
US 2010/0280269 A1    Nov. 4, 2010

(30) Foreign Application Priority Data
Dec. 28, 2007 (JP) .................. 2007-339535

(51) Int. Cl.
*C07C 51/235* (2006.01)
(52) U.S. Cl.
USPC ...................................................... 562/532
(58) Field of Classification Search
USPC ................................................ 562/538, 532
See application file for complete search history.

(56) References Cited

U.S. PATENT DOCUMENTS

| | | | |
|---|---|---|---|
| 2007/0129570 A1* | 6/2007 | Shima et al. | 562/538 |
| 2007/0167642 A1* | 7/2007 | Oku et al. | 554/174 |
| 2008/0183013 A1 | 7/2008 | Dubois et al. | |
| 2009/0134357 A1* | 5/2009 | Bub et al. | 252/194 |

FOREIGN PATENT DOCUMENTS

| | | |
|---|---|---|
| EP | 1 710 227 A1 | 10/2006 |
| EP | 2 186 790 A1 | 5/2010 |
| JP | 2002-265986 A | 9/2002 |
| JP | 2005-200398 A | 7/2005 |
| JP | 2005-213225 A | 8/2005 |
| WO | 2006/092272 A2 | 9/2006 |
| WO | 2006/114506 A1 | 11/2006 |

OTHER PUBLICATIONS

Kagaku Daijiten Henshu Iinkai. Kagaku Daijiten 3 reduced-size edition, Kyoritsu Shuppan Co., Ltd., 1963 Nen, pp. 420 to 421.
Kagaku Daijiten Henshu Iinkai. Kagaku Daijiten 9 reduced-size edition, Kyoritsu Shuppan Co., Ltd., 1964 Nen, p. 374.
European Search Report issued in Application No. 08868845.2 dated Jun. 6, 2012.

* cited by examiner

*Primary Examiner* — Taylor Victor Oh
(74) *Attorney, Agent, or Firm* — Sughrue Mion, PLLC

(57) ABSTRACT

To provide a method of producing acrylic acid which enables low energy-consumption production of acrylic acid from glycerin mixtures including glycerin and one or more compound selected from the group consisting of fatty acids, fatty acid salts, glycerides, fatty acid esters, alkali compounds and alkali compound salts. The method of producing acrylic acid according to the present invention includes the steps of obtaining an acrolein mixture by causing a dehydration reaction to a glycerin mixture; and obtaining an acrylic acid mixture by causing an oxidation reaction to the acrolein mixture; and recovering acrylic acid from the acrylic acid mixture.

12 Claims, No Drawings

METHOD FOR PRODUCTION OF ACRYLIC ACID

TECHNICAL FIELD

The present invention relates a method for the production of acrylic acid using a glycerin mixture containing glycerin as a main constituent.

BACKGROUND ART

Generally, acrylic acid is produced from oxidation of propylene which is a fossil resource. However methods of production which depend on fossil resources entail a risk of increasing atmospheric carbon dioxide. In addition, there is a risk that fossil resources will become depleted in the future.

In this regard, consideration has been given to the use of glycerin which is produced as a byproduct when producing biodiesel fuel from vegetable oils and fats or animal oils and fats, or when producing soap. In other words, consideration has been given to a method of producing acrylic acid by dehydrating and oxidizing glycerin produced as a byproduct.

There is no risk that glycerin produced from vegetable oils and fats will become a depleted resource due to its plant origin. Moreover since the carbon source is carbon dioxide in the atmosphere, there is the advantage of substantially not causing an increase in carbon dioxide in the atmosphere. Furthermore animal oils and fats are a resource which is created by the ingestion of feed such as vegetable oils and fats by livestock and therefore, the carbon source of that resource can also be treated as carbon dioxide in the atmosphere.

Known methods for producing acrylic acid from glycerin include a method for producing glycerin using a dehydration reaction and oxidation reaction of glycerin in the presence of molecular oxygen (for example, see Patent Literature 1). Furthermore in Patent Literature 2, a method of producing acrylic acid is disclosed in which glycerin is dehydrated in gaseous phase and the gaseous reactants produced by the dehydration reaction are reacted by gas-phase oxidation (for example, see Patent Literature 2). The glycerin used in these reactions normally has a high level of purity.

[Patent Literature 1] PCT International Patent Publication No. 06/114506
[Patent Literature 2] Japanese Unexamined Patent Application No. 2005-213225

DISCLOSURE OF THE INVENTION

[Problem to be Solved by the Invention]

However glycerin obtained when producing biodiesel fuel from vegetable oils and fats or animal oils and fats, or when producing soap, contains impurities including byproducts such as fatty acids, fatty acid salts, glycerides, fatty acid esters, alkali compounds or alkali compound salts. Consequently distillation is necessary in order to obtain high-purity glycerin. However the high boiling of glycerin requires large amount of energy when distilling. The reasons for use of byproduct glycerin are less convincing if large amounts of energy are consumed to enable use of the byproduct glycerin.

The above issues have resulted in a need for enabling use of glycerin produced as a byproduct during biodiesel production or soap production which is associated with low energy consumption.

The present invention is proposed to provide a method of producing acrylic acid which enables low energy-consumption production of acrylic acid from glycerin mixtures including glycerin.

[Means for Solving the Problem]

Diligent research conducted by the present inventors resulted in the insight that a dehydration reaction and oxidation reaction in the presence of one or more compound selected from the group consisting of fatty acids, fatty acid salts, glycerides, fatty acid esters, alkali compounds and alkali compound salts, resulted in production of acrylic acid with the same yield as when such compounds were not present. That insight was employed to invent a method for producing acrylic acid as described hereafter.

The present invention is configured as described hereafter.

[1]
A method of producing acrylic acid comprising the steps of:
(1) dehydrating a glycerin mixture to obtain an acrolein mixture;
(2) oxidizing the acrolein mixture to obtain an acrylic acid mixture; and
(3) recovering acrylic acid from the acrylic acid mixture.

[2]
A method of producing acrylic acid according to [1] above wherein the step (2) is executed in the presence of molecular oxygen.

[3]
A method of producing acrylic acid according to [1] above wherein step (1) and step (2) are executed simultaneously.

[4]
A method of producing acrylic acid according to [1] or [2] above wherein the steps (2) and (3) are executed simultaneously.

[5]
A method of producing acrylic acid according to any one of [1] to [4] above further comprising the step (A) of obtaining a glycerin mixture, the step (A) comprising (a) and (b) below:
(a) causing an ester substitution reaction between an oil or a fat and an alcohol to thereby obtain a fatty acid ester mixture including fatty acid esters, glycerin, fatty acids and/or fatty acid salts; and
(b) removing the fatty acid esters from the fatty acid ester mixture; and thereafter executing steps (1) to (3) above.

[6]
A method of producing acrylic acid according to [5] above wherein a part or all of a residue remaining after recovery of acrylic acid from the acrylic acid mixture is used in (A) (a) above to obtain a fatty acid ester mixture.

[7]
A method of producing acrylic acid according to [6] above wherein after a part or all of the residue remaining after recovery of acrylic acid from the acrylic acid mixture is processed with acid, the processed residue is used in (A) (a) above to obtain a fatty acid ester mixture.

[8]
A method of producing acrylic acid according to any one of [1] to [4] above further comprising the step (B) of obtaining a glycerin mixture, the step (B) comprising (c) and (d) below:
(c) causing a saponification reaction between an oil or a fat and an alkali to thereby obtain a fatty acid alkali salt mixture including fatty acid alkali salts, glycerin and fatty acids; and
(d) removing the fatty acid alkali salts from the fatty acid alkali salt mixture; and
thereafter executing steps (1) to (3) above.

[9]
A method of producing acrylic acid according to [8] above wherein a part or all of the residue remaining after recovery of acrylic acid from the acrylic acid mixture is used in (B) (c) above to obtain a fatty acid alkali salt mixture.

[10]

A method of producing acrylic acid according to any one of [1] to [9] above wherein the step (3) is executed by distillation of the acrylic acid mixture.

[11]

A method of producing acrylic acid according to any one of [1] to [10] above wherein the glycerin mixture includes one or more compound selected from the group consisting of fatty acids, fatty acid salts, glycerides, fatty acid esters, alkali compounds and alkali compound salts.

[12]

A method of producing acrylic acid according to [11] above in which the fatty acid is one or more fatty acid selected from the group of fatty acids having 4-24 carbon atoms.

[13]

A method of producing acrylic acid according to [11] above wherein the fatty acid salt is a salt of: one or more fatty acid selected from the group of fatty acids having 4-24 carbon atoms, and one or more compound selected from the group consisting of alkali metal compounds, alkali earth metal compounds and amine compounds.

[14]

A method of producing acrylic acid according to [11] above wherein the glyceride is formed from one or more fatty acid selected from the group of fatty acids having 4-24 carbon atoms.

[15]

A method of producing acrylic acid according to [11] above wherein the fatty acid ester is an ester of: one or more alcohol selected from the group of alcohols having 1-10 carbon atoms, and one or more fatty acid selected from the group of fatty acids having 4-24 carbon atoms.

[Effects of the Invention]

According to the method of producing acrylic acid in the present invention, acrylic acid can be produced with low energy consumption from a glycerin mixture including glycerin and one or more compound selected from the group of fatty acids, fatty acid salts, glycerides, fatty acid esters, alkali compounds or alkali compound salts.

DETAILED DESCRIPTION OF THE PREFERRED EMBODIMENTS

First Embodiment

A first embodiment of a method of producing acrylic acid according to the present invention will be described hereafter.

The method of producing acrylic acid according to the present embodiment comprises steps of causing an ester substitution reaction between an oil or a fat and an alcohol to thereby obtain a fatty acid ester mixture (hereafter "first step"), removing the fatty acid esters from the fatty acid ester mixture to thereby obtain a glycerin mixture (hereafter "second step"), causing a dehydration reaction to glycerin mixture to thereby obtain an acrolein mixture (hereafter "third step"), causing an oxidation reaction to the acrolein mixture to thereby obtain an acrylic acid mixture (hereafter "fourth step"), recovering acrylic acid from the acrylic acid mixture (hereafter "fifth step") and returning a part or all of the residue remaining after the fifth step to the first step (hereafter "sixth step").

(First Step)

The oil and fat used in the first step includes for example vegetable oils or fats, animal oils or fats and waste oils and fats.

The vegetable oil and fat includes for example linseed oil, safflower oil, sunflower oil, soyabean oil, maize oil, arachis oil, cottonseed oil, sesame oil, rice oil, rapeseed oil, olive oil, palm oil, coconut oil, castor oil, rice bran oil, walnut oil, camellia oil, peanut oil and the like.

Animal oils and fats include for example beef tallow, lard, mutton tallow, neat's foot oil, bird oil, chicken oil, fish oil, whale oil, butter and the like.

Waste oils and fats include animal and vegetable oils and fats which have been used in cooking processes, food processing facilities, lunch box preparation facilities, fast-food shops, restaurants or residential housing.

An oil or a fat is an ester of a fatty acid and glycerin. A fatty acid is a monovalent carboxylic acid of a long chain hydrocarbon. The long chain hydrocarbon may include double bonds. In view of application to the present invention, the fatty acid is preferably one or more fatty acid selected from the group of fatty acids having 4-24 carbon atoms. Specific examples of fatty acids having 4-24 carbon atoms include for example, butanoic acid, caproic acid, caprylic acid, capric acid, lauric acid, myristic acid, palmitic acid, stearic acid, arachic acid, behenic acid, lignoceric acid, oleic acid, cetoleic acid, erucic acid, brassidic acid, sorbic acid, linoleic acid, linolenic acid, arachidonic acid, eicosenoic acid, ricinolic acid and the like.

In view of application to the present invention, the alcohol in the first step is preferably selected from one or more of the group of alcohols having 1-10 carbon atoms. Alcohols having 1-10 carbon atoms include for example methyl alcohol, ethyl alcohol, n-propyl alcohol, iso-propyl alcohol, n-butyl alcohol, iso-butyl alcohol, sec-butyl alcohol, tert-butyl alcohol, n-pentyl alcohol, n-hexyl alcohol, n-heptyl alcohol, n-octyl alcohol, n-nonyl alcohol, n-decyl alcohol and the like.

From the point of view of productivity, when causing the ester substitution reaction, the use of a catalyst adapted to the ester substitution reaction is preferred. Catalysts adapted for ester substitution include an acid catalyst or a basic catalyst. Acid catalysts include for example, inorganic acids such as sulfuric acid, hydrochloric acid or phosphoric acid, strongly acid ion exchange resins, heteropolyacids such as tungstosilicic acid and phosphotungstic acid, zirconium oxide sulfate and the like. Basic catalysts include for example hydroxides, oxides, carbonates or alkoxides of alkali metals such as sodium, potassium, rubidium and cesium, or hydroxides, oxides, carbonates or alkoxides of alkali earth metals such as magnesium, calcium, strontium and barium, strongly basic ion exchange resins or amines.

A fatty acid ester mixture containing fatty acid esters, glycerin, fatty acids and/or fatty acid salts is obtained by causing an ester substitution reaction between an oil or a fat and an alcohol. The resulting fatty acid ester corresponds to the oil and fat and alcohol which are used, and may be used as a so-called biodiesel which is a fuel for a diesel engine.

(Second Step)

In the second step, the method of removing the fatty acid ester from the fatty acid ester mixture includes for example a method of distilling the fatty acid ester mixture, a method of liquid-liquid separation, a method of separation using a column and the like.

The glycerin mixture obtained by removing the fatty acid ester from the fatty acid ester mixture includes glycerin and one or more compound selected from the group consisting of fatty acids, fatty acid salts, glycerides, fatty acid esters, alkali compounds, and alkali compound salts.

The fatty acids contained in the glycerin mixture are the same as those fatty acids constituting the oil and fat. However the fatty acids contained in the glycerin mixture are preferably fatty acids having a boiling point at 0.10 MPa in a range of 200-400° C. Fatty acids having such a boiling point include for example, caproic acid, caprylic acid, capric acid, dodecanoic acid, myristic acid, palmitic acid, stearic acid, oleic acid, linoleic acid, linolenic acid and ricinoleic acid. Although there are difficulties associated with separation using distillation of these fatty acids due to a boiling point close to that of glycerin, separation is facilitated by transforming glycerin into acrylic acid.

The fatty acid salts contained in the glycerin is a salt of one or more fatty acid selected from the above group of fatty acids having 4-24 carbon atoms and one or more compound selected from the group consisting of alkali metal compounds, alkali earth metal compounds and amine compounds.

Alkali metal compounds include hydroxides, oxides, carbonates or alkoxides of alkali metals such as sodium, potassium, rubidium, cesium and the like. Alkali earth metal compounds include hydroxides, oxides, carbonates or alkoxides of alkali earth metals such as magnesium, calcium, strontium, barium and the like.

The amine compound includes ammonia, methylamine, dimethylamine, trimethylamine, ethylamine, diethylamine, triethylamine, propylamine, dipropylamine, tripropylamine, butylamine, dibutylamine, tributylamine, aniline, ethylene diamine, diethylene triamine, pyrrole, pyridine, tetramethylammonium hydroxide, tetraethylammonium hydroxide, tetrapropylammonium hydroxide, tetrabutylammonium hydroxide, urea and the like.

The glycerin content of the glycerin mixture obtained by removing fatty acid esters from the fatty acid ester mixture is preferably 5-95 mass %, more preferably 10-95 mass % and still more preferably 15-95 mass %. From the point of view of sufficiently maintaining the yield of acrylic acid, the content of glycerin is preferably 5 mass % or more, and when less than or equal to 95 mass %, the utility of the present invention is improved.

The content of fatty acids in the glycerin mixture when the glycerin content (mass) is taken to be 1 preferably has a mass ratio of 0.001-1, and more preferably 0.01-0.1. If the content of fatty acids is 0.001 or less when the glycerin content is taken to be 1, the utility of the present invention exhibits a tendency to decrease and when the value exceeds 1, the yield of acrylic acid is low and the efficiency tends to decrease.

When the glycerin content (mass) is taken to be 1, the content of fatty acid salts in the glycerin mixture preferably has a mass ratio of 0.001-1 and more preferably 0.01-0.1. If the content of fatty acid salts is 0.001 or less when the glycerin content is taken to be 1, the utility of the present invention exhibits a tendency to decrease and when the value exceeds 1, the yield of acrylic acid is low and the efficiency tends to decrease.

The glyceride includes any of a monoglyceride, diglyceride or triglyceride. The fatty acids constituting the glycerides are the same as the fatty acids which constitute the oil and fat above.

When the glycerin content (mass) is taken to be 1, the glyceride content in the glycerin mixture preferably has a mass ratio of 0.001-1 and more preferably 0.01-0.5. If the glyceride content is 0.001 or less when the glycerin content is taken to be 1, the utility of the present invention exhibits a tendency to decrease and when the value exceeds 1, the yield of acrylic acid is low and the efficiency tends to decrease.

The alkali compounds include hydroxides, oxides, carbonates or alkoxides of sodium, potassium, rubidium, cesium and the like, or hydroxides, oxides, carbonates or alkoxides of alkali earth metals such as magnesium, calcium, strontium, barium and the like, strongly basic ion exchange resins or amines and the like.

The content of alkali compounds in the glycerin mixture when the glycerin content (mass) is taken to be 1 preferably has a mass ratio of 0.001-1 and more preferably 0.01-0.5. If the content of alkali compounds is 0.001 or less when the glycerin content is taken to be 1, the utility of the present invention exhibits a tendency to decrease and, when the value exceeds 1, the yield of acrylic acid is low and the efficiency tends to decrease.

The salt of the alkali compound includes an acidic salt or neutral salt of an alkali compound and an acid. The acid includes for example sulfuric acid, hydrochloric acid, phosphoric acid, nitric acid, boric acid and the like.

The content of alkali compound salts in the glycerin mixture when the glycerin content (mass) is taken to be 1 preferably has a mass ratio of 0.001-1 and more preferably 0.01-0.5. If the content of alkali compound salts is 0.001 or less when the glycerin content is taken to be 1, the utility of the present invention exhibits a tendency to decrease and, when the value exceeds 1, the yield of acrylic acid is low and the efficiency tends to decrease.

In addition to glycerin, fatty acids, fatty acid salts, glycerides, fatty acid esters, alkali compounds or alkali compound salts, the glycerin mixture may, for example, include a constituent such as water, a base, an acid or an alcohol. Furthermore the glycerin mixture may be diluted using a solvent (for example, water) which does not have an adverse effect on reactions in or after the third step.

(Third Step)

More specifically, in the third step, glycerin mixture is subjected to a dehydration reaction to thereby obtain an acrolein mixture.

The dehydration reaction preferably uses a dehydration reaction catalyst in order to increase the reaction speed. The dehydration reaction catalyst includes an acid catalyst or basic catalyst. The acid catalyst includes for example natural or synthetic clay compounds such as kaolinite, bentonite, montmorillonite, zeolite and the like, oxides/composite oxides such as silica, alumina, titania, zirconia, and silica-aluminia, heteropolyacids, sulfates, sulfate acid salts, carbonates, carbonic acid salts, nitrates, nitrate acid salts, phosphates, phosphate acid salts, sulfuric acid, phosphoric acid, acid-ion exchange resins and the like.

Further examples include use of a support catalyst to support heteropolyacids, sulfates, sulfate acid salts, carbonates, carbonic acid salts, nitrates, nitrate acid salts, phosphates, phosphate acid salts, sulfuric acid, phosphoric acid and the like on a support. The support includes for example oxides/composite oxides such as silica, alumina, titania, zirconia, and silica-aluminia.

There is no particular limitation on the form of the catalyst and, for example, it includes a particulate form, a spherical form, a cylindrical form, a saddle-shaped form, a honeycomb form and the like.

The method of preparing the catalyst includes for example impregnation, precipitation, ion exchange methods and the like.

The catalyst may be fired in advance in a gas in response to a purpose therefor. The gas includes for example nitrogen, argon, helium, air and the like.

The method of manufacturing acrylic acid according to the present embodiment is a method of obtaining acrylic acid by reacting molecular oxygen with a component resulting from the above dehydration reaction.

The form of the dehydration reaction may be executed for example using either a liquid phase reaction or a gaseous phase reaction and applying a fixed bed, fluid bed and the like. A batch, semi-batch or continuous method may be employed.

The temperature of the dehydration reaction may be 0-600° C. In view of increasing the reaction efficiency, a range of 100-500° C. is preferred, and 150-400° C. is more preferred.

Since the dehydration reaction of glycerin is a reaction associated with an increase in the mole number, decreasing the pressure increases the glycerin yield. More specifically, a pressure of 0.01-10.0 MPa is preferred, and 0.05-5 MPa more preferred.

However when using a liquid phase reaction, a temperature and a pressure are selected to enable glycerin to exist in a liquid state. When using a gaseous phase reaction, a temperature and pressure are selected to enable glycerin to exist in a gaseous state.

When using a liquid phase reaction, a catalyst may be used. The catalyst is preferably stable at the reaction temperature. This type of catalyst includes for example saturated hydrocarbons such as liquid paraffin, paraffin wax, dodecane, tridecane, tetradecane, hexadecane and the like, aromatic hydrocarbons such as dibenzy and the like, diphenyl ether, sulfolane, silicone oil and the like.

When using a gaseous phase reaction, the reaction may be diluted using an inert gas. The inert gas includes for example nitrogen, carbon dioxide, a noble gas (for example, helium, argon and the like), water vapor and the like.

(Fourth Step)

More specifically, the fourth step causes an oxidation reaction to the acrolein in the acrolein mixture to thereby obtain an acrylic acid mixture.

The oxidation reaction preferably uses an oxidation reaction catalyst in order to increase the reaction speed. The oxidation reaction catalyst includes for example a solid catalyst including a metallic oxide, and mixtures and composite oxides thereof and the like. The metal constituting the metal oxide is one or more metal selected from the group consisting of iron, molybdenum, titania, vanadium, tungsten, antimony, tin and copper.

The oxidation catalyst may be a support catalyst configured to support the oxide above on a support. The support includes silica, alumina, zirconia, and mixtures or oxide composites thereof, silicon carbide and the like.

There is no particular limitation on the form of the catalyst and, for example, it includes a particulate form, a spherical form, a cylindrical form, a saddle-shaped form, a honeycomb form and the like.

The method of preparing the catalyst includes for example impregnation, precipitation, ion exchange methods and the like.

The catalyst may be fired in a gas in advance in response to a purpose therefor. The gas includes for example nitrogen, argon, helium, air and the like.

The form of the oxidation reaction may be executed for example using either a liquid phase reaction or a gaseous phase reaction and applying a fixed bed, fluid bed and the like. A batch, semi-batch or continuous method may be employed.

In view of increasing the reaction efficiency, the temperature of the oxidation reaction is preferably 150-400° C., and 200-350° C. is more preferred.

A pressure of 0.01-10.0 MPa is preferred, and 0.05-10 MPa being more preferred.

However when using a liquid phase reaction, a temperature and pressure are selected to enable acrolein to exist in a liquid state. When using a gaseous phase reaction, a temperature and pressure are selected to enable acrolein to exist in a gaseous state.

When using a liquid phase reaction, a catalyst may be used. The catalyst is preferably stable at the reaction temperature. This type of catalyst includes for example saturated hydrocarbons such as liquid paraffin, paraffin wax, dodecane, tridecane, tetradecane, hexadecane and the like, aromatic hydrocarbons such as dibenzy and the like, diphenyl ether, sulfolane, silicone oil and the like.

The oxidation reaction is performed in the presence of molecular oxygen. The molecular oxygen may be supplied in the form of oxygen gas, or may be supplied as air. The supply of molecular oxygen may be executed between the dehydration reaction and oxidation reaction, or before the dehydration reaction.

When executing the oxidation reaction, an inert gas may be added. The inert gas includes for example nitrogen, carbon dioxide, a noble gas (for example, helium, argon and the like), water vapor and the like.

The gas composition during the oxidation reaction must be adjusted to avoid a explosion range. This type of composition includes a composition of 1-15 volume % of acrolein, 0.5-25 volume % of oxygen, 0-50 volume % of water vapor and 20-80 volume % of nitrogen.

The third step and the fourth step in the present invention may be executed simultaneously. For example, a single reaction vessel may be used to execute the dehydration reaction and the oxidation reaction simultaneously.

The reaction preferably uses a catalyst to increase the reaction speed. The catalyst may be used by mixing a dehydration reaction catalyst and an oxidation reaction catalyst. In addition, a catalyst may be used which has both dehydration and oxidation properties.

The dehydration reaction catalyst includes an acid catalyst or basic catalyst. The acid catalyst includes for example natural or synthetic clay compounds such as kaolinite, bentonite, montmorillonite, zeolite and the like, oxides/composite oxides such as silica, alumina, titania, zirconia, and silica-aluminia, heteropolyacids, sulfates, sulfate acid salts, carbonates, carbonic acid salts, nitrates, nitrate acid salts, phosphates, phosphate acid salts, sulfuric acid, phosphoric acid, acid-ion exchange resins and the like.

Further examples include use of a support catalyst supporting heteropolyacids, sulfates, sulfate acid salts, carbonates, carbonic acid salts, nitrates, nitrate acid salts, phosphates, phosphate acid salts, sulfuric acid, phosphoric acid and the like on a support. The support includes for example oxides of silica, alumina, titania, zirconia, silica-aluminia, composite oxides and the like.

There is no particular limitation on the form of the catalyst and, for example, it includes a particulate form, a spherical form, a cylindrical form, a saddle-shaped form, a honeycomb form and the like.

The method of preparing the catalyst includes for example impregnation, precipitation, ion exchange methods and the like.

The catalyst may be fired in a gas in advance in response to a purpose therefor. The gas includes for example nitrogen, argon, helium, air and the like.

The method of manufacturing acrylic acid according to the present embodiment is a method of obtaining acrylic acid by reacting molecular oxygen with a component resulting from the above dehydration reaction.

The oxidation reaction catalyst includes for example a solid catalyst including a metallic oxide, and mixtures and composite oxides thereof and the like. The metal constituting the metal oxide is one or more metal selected from the group consisting of iron, molybdenum, titania, vanadium, tungsten, antimony, tin and copper.

The oxidation catalyst may be a support catalyst configured to support the oxide above on a support. The support includes silica, alumina, zirconia, and mixtures or oxide composites thereof, silicon carbide and the like.

There is no particular limitation on the form of the catalyst and, for example, it includes a particulate form, a spherical form, a cylindrical form, a saddle-shaped form, a honeycomb form and the like.

The method of preparing the catalyst includes for example impregnation, precipitation, ion exchange methods and the like.

The catalyst may be fired in a gas in advance in response to a purpose therefor. The gas includes for example nitrogen, argon, helium, air and the like.

The form of the dehydration reaction may be executed for example using either a liquid phase reaction or a gaseous phase reaction and applying a fixed bed, fluid bed and the like. A batch, semi-batch or continuous method may be employed.

In view of increasing the reaction efficiency, the temperature of the oxidation reaction is preferably 150-400° C., and 200-350° C. is more preferred.

A pressure of 0.01-10.0 MPa is preferred, and 0.05-10 MPa being more preferred.

However when using a liquid phase reaction, a temperature and pressure are selected to enable glycerin to exist in a liquid state. When using a gaseous phase reaction, a temperature and pressure are selected to enable glycerin to exist in a gaseous state.

When using a liquid phase reaction, a catalyst may be used. The catalyst is preferably stable at the reaction temperature. This type of catalyst includes for example saturated hydrocarbons such as liquid paraffin, paraffin wax, dodecane, tridecane, tetradecane, hexadecane and the like, aromatic hydrocarbons such as dibenzy and the like, diphenyl ether, sulfolane, silicone oil and the like.

The oxidation reaction is performed in the presence of molecular oxygen. The molecular oxygen may be supplied in the form of oxygen gas, or may be supplied as air.

When executing the reaction, an inert gas may be added. The inert gas includes for example nitrogen, carbon dioxide, a noble gas (for example, helium, argon and the like), water vapor and the like.

The gas composition during the oxidation reaction must be adjusted to avoid a flammable range. This type of composition includes a composition of 1-20 volume % of glycerin, 0.5-25 volume % of oxygen, 0-50 volume % of water vapor and 20-80 volume % of nitrogen.

In order to prevent polymerization in the acrylic acid mixture obtained from the oxidation reaction, it is preferred to add a polymerization inhibitor. The polymerization inhibitor includes for example phenol compounds such as phenothiazine, phenol, hydroquinone, methoquinone, catechol, creosol and the like.

The added amount of the polymerization inhibitor when adding a polymerization inhibitor is preferably 1 mass ppm-1 mass % when acrylic acid is taken to have a mass percent of 100.

(Fifth Step)

Although the method of recovering acrylic acid from the acrylic acid mixture may apply a known separation or recovery method, a distillation method of the acrylic acid mixture is preferred for industrial level recovery.

A specific example of distillation includes simple distillation, multistage distillation, steam distillation, flash distillation and the like. The method of distillation may be a batch method, semi-batch method or a continuous method.

When using multistage distillation, distillate components having a lower boiling point than acrylic acid can be removed from the column top, acrylic acid distillate can be removed from the intermediate portion and compounds selected from fatty acids, fatty acid salts, glycerides, fatty acid esters, alkali compounds and alkali salts can be removed from the column bottom.

The distillation column used in the multistage distillation may be a known distillation column such as a tray-type distillation column, a packed distillation column and the like.

The structure of the tray used in the tray-type distillation column includes for example a bubble tray, a sieve tray, a valve tray, a super-flux tray, a max-flux tray and the like.

The packing material for the packed distillation column includes structured packing and random packing. The structured packing includes for example a metal-plate type, a metal-wire type and a grid-type. The random packing includes for example a Raschig ring, a Lessing ring, a Berl saddle, an Intalox saddle, a Tellerette, a Pall saddle, a flexiring, a cascade ring and the like.

When applying a multistage distillation to an acrylic acid mixture, the distillation conditions preferably adapt the temperature of the column bottom to be 0-120° C., more preferably 5-100° C., and still more preferably 10-80° C. When the temperature of the column bottom is more than 120° C., the acrylic acid polymerizes. When the temperature of the column bottom is less than 0° C., there is a tendency for the energy required for cooling operations to increase. The distillation pressure is determined with reference to the relationship with the temperature.

When distilling an acrylic acid mixture, polymerization of the acrylic acid is preferably prevented by addition in advance of a polymerization inhibitor. The polymerization inhibitor includes for example phenol compounds such as phenothiazine, phenol, hydroquinone, methoquinone, catechol, creosol and the like. The added amount of the polymerization inhibitor when adding a polymerization inhibitor is preferably 1 mass ppm-1 mass % when acrylic acid is taken to have a mass percent of 100.

(Sixth Step)

The residue remaining after the fifth step includes glycerin and one or more compound selected from the group consisting of fatty acids, fatty acid salts, glycerides, fatty acid esters, alkali compounds and alkali compound salts. When returning a part of the residue, a part of the residue containing a fatty acids, fatty acid salts, and glycerides may be returned, only fatty acids may be returned, only fatty acid salts may be returned and only glycerides may be returned.

When returning a part or whole of the residue to the first step, or when returning fatty acids in the residue, a fatty acid ester is produced by an esterification reaction between the fatty acid and an alcohol. This is due to the fact that the ester substitution reaction catalyst also functions as an esterification reaction catalyst.

When the fatty acid salt in the residue is returned to the first step, it may be used in a reaction with an oil or a fat. Furthermore when the fatty acid salt is returned to the first step, since a fatty acid ester is easily obtained, it is preferred to pre-process the fatty acid salt with acid prior to the first step.

The third step and the fourth step may be performed simultaneously or in sequence. When performed in sequence, a tandem reaction vessel provided with two connected reaction vessels is used to execute the dehydration reaction in the first-stage reaction vessel (third step) and the oxidation reaction (fourth step) in the second-stage reaction vessel.

The fourth step and the fifth step may be performed simultaneously or in sequence.

Second Embodiment

A second embodiment of a method for producing acrylic acid according to the present invention will be described hereafter.

The method for producing acrylic acid according to the present embodiment includes a step of causing a saponification reaction between an oil or a fat and an alkali to obtain a mixture of a fatty acid alkali salt (hereafter a first' step), a step of removing the fatty acid alkali salt from the fatty acid alkali salt mixture to obtain a glycerin mixture (hereafter a second' step), a step of subjecting the glycerin mixture to a dehydration reaction to obtain an acrolein mixture (hereafter a third step), a step of subjecting the acrolein mixture to an oxidation reaction to obtain an acrylic acid mixture (hereafter a fourth step), a step of recovering acrylic acid from the acrylic acid mixture (hereafter a fifth step), and a step of returning a part or the whole of the residue remaining after the fifth step to the first' step (hereafter a sixth' step).

(First' Step)

The oil and fat used in the first' step may be the same as the oil and fat used in the first embodiment.

In the first' step, the alkali compound reacted with the oil and fat includes hydroxides, oxides, carbonates or alkoxides of alkali metals such as sodium, potassium, rubidium, cesium and the like, or hydroxides, oxides, carbonates or alkoxides of alkali earth metals such as magnesium, calcium, strontium, barium and the like; strongly basic ion exchange resins, amines and the like.

The reaction between the oil and fat and the alkali may be executed using a known method. The fatty acid alkali salt mixture resulting from this reaction includes fatty acids and/or fatty acid salts, glycerin, and fatty acid alkali salts corresponding to the alkali.

The fatty acid alkali salt includes for example sodium fatty acids, potassium fatty acids, magnesium fatty acids, calcium fatty acids and the like. These fatty acid alkali salts can be used as a soap.

(Second' Step)

In the second' step, a method of removing a fatty acid alkali salt from the fatty acid alkali salt mixture for example is the same as the method of removing the fatty acid ester from the fatty acid ester mixture in the first embodiment.

In the glycerin mixture obtained by removing the fatty acid alkali salt from the fatty acid alkali salt mixture, the preferred range of the glycerin content, the content of fatty acid salts and the content of fatty acids in the glycerin mixture are the same as in the first embodiment.

In addition to glycerin, fatty acids and fatty acid salts, the glycerin mixture according to the present embodiment may, for example, include a constituent such as water, a base, an acid, a fatty acid ester, an alcohol, glyceride and the like. Furthermore the glycerin mixture may be diluted using a solvent (for example, water) which does not have an adverse effect on reactions in or after the third step.

(Third Step, Fourth Step, Fifth Step)

The third step, fourth step and fifth step are the same as the first embodiment.

(Sixth' Step)

In the sixth' step, a part or the whole of the residue remaining after the fifth step, in other words, the fatty acids are returned to the first' step to thereby enable production of a saponification reaction with an alkali.

The present embodiment also preferably uses an acid to pre-process the fatty acid salt prior to the first' step when returning the fatty acid salt to the first' step.

In the method of production of acrylic acid according to the first embodiment and the second embodiment as described above, the glycerin mixture is supplied to the dehydration and oxidation reaction without distillation which thereby suppresses energy consumption when using a glycerin mixture.

However energy consumption increases when separating glycerin having a high boiling point (boiling point at 0.1 MPa: 290° C.) and one or more compound selected from the group consisting of fatty acids, fatty acid salts, glycerides, fatty acid esters, alkali compounds and alkali compound salts. However in the production method according to the present embodiment, when separating glycerin and acrylic acid having a low boiling point (boiling point at 0.1 MPa: 139° C.) and one or more compound selected from the group consisting of fatty acids, fatty acid salts, glycerides, fatty acid esters, alkali compounds and alkali compound salts, energy consumption is low since only the low-boiling point acrylic acid needs to be extracted by distillation.

Thus the production method above enables production of acrylic acid from a glycerin mixture using low energy consumption.

In the above embodiments, in the sixth step or the sixth' step, since the residue remaining after the fifth step is returned to the first' step, the yield of the fatty acid ester against the oil and fat standard can be increased.

The method of producing acrylic acid according to the present invention is not limited to the first embodiment and the second embodiment. In the embodiments above, although a part or the whole of the residue remaining after the fifth step was returned to the first step, a fatty acid ester may be produced by reacting the fatty acid remaining after the fifth step with an alcohol without returning a residue to the first step.

The alcohol may be the same as the alcohol used in the first step. When reacting the fatty acid with the alcohol, it is preferred to use an esterification reaction catalyst. The esterification reaction catalyst includes an acid catalyst or basic catalyst. The acid catalyst includes for example, inorganic acids such as sulfuric acid, hydrochloric acid or phosphoric acid, strongly acid ion exchange resins, heteropolyacids such as tungstosilicic acid, phosphotungstic acid and the like, zirconium oxide sulfate and the like. The basic catalyst includes for example hydroxides, oxides, carbonates or alkoxides of alkali metals such as sodium, potassium, rubidium, cesium and the like, or hydroxides, oxides, carbonates or alkoxides of alkali earth metals such as magnesium, calcium, strontium, barium and the like, strongly basic ion exchange resins, amines and the like.

The alkali may be reacted with fatty acid remaining after the fifth step to produce a fatty acid alkali.

An alkali used when producing a fatty acid alkali salt for example includes hydroxides or carbonates of sodium, potassium, magnesium, calcium and the like. These fatty acid alkali salts may be used as a soap.

The present invention will be described in further detail hereafter making reference to the embodiments. However the present invention is not limited only to the embodiments.

PREPARATION EXAMPLE 1

Preparation of Catalyst A 6 g of potassium hydrogen sulfate was dissolved in water to prepare an aqueous solution of potassium hydrogen sulfate. 14 g of silica were introduced into the aqueous solution of potassium hydrogen sulfate, dried and fired for three hours at a temperature of 300° C. in an atmosphere of nitrogen to thereby obtain a dehydration reaction catalyst A constituted by potassium acid sulfate/silica.

PREPARATION EXAMPLE 2

Preparation of Catalyst B 7.0 g of ammonium paramolybdate, 2.1 g of ammonium metavanadate, 0.89 g of ammonium paratungstate and 50 m of water were placed in a flask, stirred while heating to 90° C. and dissolved. An aqueous solution of copper nitrate prepared in advance by dissolving 1.8 g of copper nitrate in 15 ml of water was added to the solution above to thereby prepare a catalyst preparation solution.

The catalyst preparation solution was saturated with 20 g of α-alumina and then evaporated to dryness. After drying, firing was performed for three hours at 400° C. in an atmosphere of air to thereby obtain an oxidation reaction catalyst B constituted by an α-alumina carrier of a molybdenum-vanadium-tungsten-copper oxide.

COMPARATIVE EXAMPLE 1

Recovery of Glycerin 500 g of a glycerin mixture containing 60 mass % of glycerin, 3.0 mass % of palmitic acid, 2.7 mass % of oleic acid, 2.7 mass % of monoglyceride palmitate, 2.7 mass % of monoglyceride oleate, 2.1 mass % of methyl palmitate, 1.8 mass % of methyl oleate, 9.7 mass % of water and 15.3 mass % of other components was introduced into a 1000 ml flask provided with a fractionating column and distilled under reduced pressure to thereby obtain a glycerin distillate. The recovered amount in the distillate liquid was 291 g. Gas chromatography analysis of the distillate liquid shows a glycerin composition ratio of 98 mass %. The presence of palmitic acid, oleic acid, monoglyceride palmitate, monoglyceride oleate, methyl palmitate and methyl oleate could not be confirmed. The yield of glycerin in the distillate relative to the introduced glycerin was 95%.

[Reaction]

Two stainless steel reaction tubes having an inner diameter of 10 mm and a length of 300 mm were connected and an electric furnace was mounted on each reaction tube to prepare a reaction device. The first-stage reaction tube in the reaction device was filled with 5 ml of catalyst A prepared in Preparation Example 1 and the second-stage reaction tube was filled with 5 ml of catalyst B prepared in Preparation Example 2. Piping was connected to enable the addition of gas between the first-stage reaction tube and the second-stage reaction tube.

A 20 mass % glycerin aqueous solution of glycerin obtained as above diluted using water was supplied continuously at a rate of 8 g/hour to the first-stage reaction tube. The first-stage reaction tube was heated to 300° C. in the electric furnace and the second-stage reaction tube was heated to 280° C. in the electric furnace. Oxygen was supplied at a rate of 600 Nml/hour between the first-stage reaction tube and the second-stage reaction tube.

The exit port of the second-stage reaction tube was cooled and the resulting reaction gas was condensed and collected. Gas chromatograph analysis of the collected liquid (collection liquid) showed that glycerin conversion was 100% and acrylic acid yield was 51%.

Then the collection liquid was subjected to precision distillation to obtain purified acrylic acid. The acrylic acid yield of acrylic acid against the glycerin standard after purification was 45%.

EXAMPLE 1

[Reaction]

Using the same reaction device as the comparative example, the first-stage reaction tube was filled with 5 ml of catalyst A prepared in Preparation Example 1 and the second-stage reaction tube was filled with 5 ml of catalyst B prepared in Preparation Example 2.

A glycerin mixture containing 20 mass % of glycerin, 1.0 mass % of palmitic acid, 0.9 mass % of oleic acid, 0.9 mass % of monoglyceride palmitate, 0.8 mass % of monoglyceride oleate, 0.7 mass % of methyl palmitate, 0.6 mass % of methyl oleate, 70 mass % of water and 5.1 mass % of other components was supplied at a rate of 8 g/hour to the first-stage reaction vessel. The first-stage reaction tube was heated to 300° C. in the electric furnace and the second-stage reaction tube was heated to 280° C. in the electric furnace. Oxygen was supplied at a rate of 600 Nml/hour between the first-stage reaction tube and the second-stage reaction tube.

The exit port of the second-stage reaction tube was cooled and the reaction gas was condensed and collected. Gas chromatograph analysis of the collection liquid showed that glycerin conversion was 100% and acrylic acid yield was 51%.

Then the collection liquid was subjected to precision distillation to obtain purified acrylic acid. The acrylic acid yield of acrylic acid against the glycerin standard after purification was 48%.

In the present embodiment, even though the glycerin mixture was not distilled, acrolein was obtained at an equivalent yield to the Comparative Example 1 which distilled and purified a glycerin mixture.

Furthermore since acrylic acid was obtained at an equivalent yield to the Comparative Example 1 without distillation of the glycerin mixture, it is shown that acrylic acid can be manufactured with low energy consumption per unit amount of acrylic acid.

COMPARATIVE EXAMPLE 2

[Reaction]

5 ml of components of the catalyst A obtained in Preparation Example 1 sifted to have a particle diameter of 0.5-1.0 mm and 5 ml of the catalyst B obtained in Preparation Example 2 were substantially mixed. The resulting catalyst mixture was used to fill a stainless steel reaction tube having an inner diameter of 10 mm and a length of 300 mm.

Then the reaction tube was heated to 300° C. to create a reaction while supplying a 20 mass % glycerin aqueous solution as in Comparative Example 1 at a rate of 8 g/hour and oxygen at a rate of 600 Nml/hour.

The exit port of the reaction tube was cooled, and the reaction gas was condensed and collected. Gas chromatograph analysis of the collection liquid showed that glycerin conversion was 100% and acrylic acid yield was 45%.

Then the collection liquid was subjected to precision distillation to obtain purified acrylic acid. The acrylic acid yield of acrylic acid against the glycerin standard after purification was 43%.

EXAMPLE 2

[Reaction]

In the Comparative Example 2, a glycerin mixture containing 20 mass % of glycerin, 1.0 mass % of palmitic acid, 0.9 mass % of oleic acid, 0.9 mass % of monoglyceride palmitate, 0.8 mass % of monoglyceride oleate, 0.7 mass % of methyl palmitate, 0.6 mass % of methyl oleate, 70 mass % of water and 5.1 mass % of other components was substituted for the 20 mass % glycerin aqueous solution in Comparative Example 2 and supplied to the reaction tube. In other respects, the reaction was the same as Comparative Example 2.

The exit port of the reaction tube was cooled, and the reaction gas was condensed and collected. Gas chromatograph analysis of the collection liquid showed that glycerin conversion was 100% and acrylic acid yield was 45%.

Then the collection liquid was subjected to precision distillation to obtain purified acrylic acid. The acrylic acid yield of acrylic acid against the glycerin standard after purification was 43%.

In the present embodiment, even though the glycerin mixture was not distilled, acrylic acid was obtained at an equivalent yield to the Comparative Example 2 which distilled and purified a glycerin mixture. Thus it is shown that acrylic acid can be manufactured with low energy consumption per unit amount of acrylic acid.

[Industrial Applicability]

According to the method for preparation of acrylic acid of the present invention, acrylic acid can be prepared with low energy consumption from a glycerin mixture including glycerin and one or more compound selected from the group consisting of fatty acids, fatty acid salts, glycerides, fatty acid esters, alkali compounds and alkali compound salts.

The invention claimed is:

1. A method of producing acrylic acid comprising:
    (1) obtaining a glycerin mixture by:
        (a) causing an ester substitution reaction between an oil or a fat and an alcohol to thereby obtain a fatty acid ester mixture including at least three of fatty acid esters, glycerin, fatty acids or fatty acid salts; and
        (b) removing the fatty acid esters from the fatty acid ester mixture; or
        (c) causing a saponification reaction between an oil or a fat and an alkali to thereby obtain a fatty acid alkali salt mixture including fatty acid alkali salts, glycerin and fatty acids; and
        (d) removing the fatty acid alkali salts from the fatty acid alkali salt mixture;
    (2) dehydrating the glycerin mixture to obtain an acrolein mixture;
    (3) oxidizing the acrolein mixture to obtain an acrylic acid mixture; and
    (4) recovering acrylic acid from the acrylic acid mixture.

2. The method of producing acrylic acid according to claim 1 wherein the oxidizing of the acrolein mixture is executed in the presence of molecular oxygen.

3. The method of producing acrylic acid according to claim 1 wherein the dehydrating of a glycerin mixture and the oxidizing of the acrolein mixture are executed simultaneously.

4. The method of producing acrylic acid according to claim 1 wherein the oxidizing of the acrolein mixture and recovering of acrylic acid are executed simultaneously.

5. The method of producing acrylic acid according to claim 1 wherein a part or all of a residue remaining after recovery of acrylic acid from an acrylic acid mixture is used in the causing of an ester substitution reaction to obtain a fatty acid ester mixture.

6. The method of producing acrylic acid according to claim 5 wherein after a part or all of the residue remaining after recovery of acrylic acid from an acrylic acid mixture is processed with acid, the processed residue is used in the causing of an ester substitution reaction to obtain a fatty acid ester mixture.

7. The method of producing acrylic acid according to claim 1 wherein a part or all of the residue remaining after recovery of acrylic acid from the acrylic acid mixture is used in (1)(c) above to obtain a fatty acid alkali salt mixture.

8. The method of producing acrylic acid according to claim 1 wherein the (4) is executed by distillation of the acrylic acid mixture.

9. The method of producing acrylic acid according claim 1 wherein the fatty acid is one or more fatty acids selected from the group of fatty acids having 4-24 carbon atoms.

10. The method of producing acrylic acid according claim 1 wherein the fatty acid salt is a salt of: one or more fatty acids selected from the group of fatty acids having 4-24 carbon atoms, and one or more compounds selected from the group consisting of alkali metal compounds, alkali earth metal compounds and amine compounds.

11. The method of producing acrylic acid according claim 1 wherein the glyceride is formed from one or more fatty acids selected from the group of fatty acids having 4-24 carbon atoms.

12. The method of producing acrylic acid according claim 1 wherein the fatty acid ester is an ester of: one or more alcohols selected from the group of alcohols having 1-10 carbon atoms, and one or more fatty acids selected from the group of fatty acids having 4-24 carbon atoms.

* * * * *